(12) United States Patent
Araki et al.

(10) Patent No.: US 11,607,394 B2
(45) Date of Patent: Mar. 21, 2023

(54) ROTIGOTINE-CONTAINING PATCH

(71) Applicant: HISAMITSU PHARMACEUTICAL CO., INC., Tosu (JP)

(72) Inventors: Hiroyuki Araki, Tsukuba (JP); Yuka Takagi, Tsukuba (JP); Yoko Fujiwara, Tsukuba (JP); Hiroaki Kobayashi, Tsukuba (JP); Takao Kurokawa, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 240 days.

(21) Appl. No.: 16/954,627

(22) PCT Filed: Dec. 14, 2018

(86) PCT No.: PCT/JP2018/046137
§ 371 (c)(1),
(2) Date: Jun. 17, 2020

(87) PCT Pub. No.: WO2019/124261
PCT Pub. Date: Jun. 27, 2019

(65) Prior Publication Data
US 2020/0306203 A1    Oct. 1, 2020

(30) Foreign Application Priority Data

Dec. 19, 2017 (JP) .............................. JP2017-242845
Jul. 31, 2018 (JP) .............................. JP2018-143868

(51) Int. Cl.
| A61P 25/16 | (2006.01) |
| A61K 47/32 | (2006.01) |
| A61K 31/381 | (2006.01) |
| A61K 9/70 | (2006.01) |

(52) U.S. Cl.
CPC .......... *A61K 9/7053* (2013.01); *A61K 9/7076* (2013.01); *A61K 31/381* (2013.01)

(58) Field of Classification Search
CPC .. A61K 9/7053; A61K 9/7076; A61K 31/381; A61K 47/32; A61P 25/16; A61P 25/14
See application file for complete search history.

(56) References Cited

U.S. PATENT DOCUMENTS

| 6,884,434 B1 | 4/2005 | Muller et al. |
| 9,408,802 B1 | 8/2016 | Hartwig |
| 2005/0033065 A1 | 2/2005 | Mueller et al. |
| 2005/0175678 A1 | 8/2005 | Breitenbach |
| 2008/0050424 A1 | 2/2008 | Muller et al. |
| 2008/0089926 A1 | 4/2008 | Ishima et al. |
| 2008/0138389 A1 | 6/2008 | Muller et al. |
| 2009/0143460 A1 | 6/2009 | Wolff et al. |
| 2010/0086582 A1 | 4/2010 | Tang et al. |
| 2010/0311806 A1 | 12/2010 | Wolff et al. |
| 2011/0165247 A1 | 7/2011 | Breitenbach |
| 2012/0213912 A1 | 8/2012 | Leonhard et al. |
| 2012/0322845 A1 | 12/2012 | Wolff et al. |
| 2014/0046279 A1 | 2/2014 | Leonhard et al. |
| 2014/0378917 A1 | 12/2014 | Dzekan et al. |
| 2015/0231255 A1 | 8/2015 | Yoshinaga et al. |
| 2017/0128413 A1 | 5/2017 | Youn et al. |
| 2018/0147154 A1 | 5/2018 | Wolff et al. |
| 2018/0263921 A1 | 9/2018 | Wolff et al. |
| 2019/0314294 A1 | 10/2019 | Wolff et al. |
| 2019/0328680 A1 | 10/2019 | Dzekan et al. |

FOREIGN PATENT DOCUMENTS

| EP | 2799480 | * | 5/2014 |
| JP | 2002-509878 A | | 4/2002 |
| JP | 2006-513195 A | | 4/2006 |
| JP | 2008-522957 A | | 7/2008 |
| JP | 2011-504902 A | | 2/2011 |
| JP | 2012-504609 A | | 2/2012 |
| JP | 2013-510805 A | | 3/2013 |
| JP | 2013-79220 A | | 5/2013 |
| JP | 2013-515041 A | | 5/2013 |

(Continued)

OTHER PUBLICATIONS

Polymer Database on SEBS (pp. 1-2, Accessed on Aug. 8, 2022, Accessed from https://polymerdatabase.com/Polymer%20Brands/SEBS.html). (Year: 2022).*
International Search Report in International Application No. PCT/JP2018/046137, dated Feb. 26, 2019.
International Preliminary Report on Patentability dated Jun. 23, 2020 with Written Opinion from the International Bureau in International Application No. PCT/JP2018/046137.
Extended European Search Report dated Nov. 6, 2020 in European Application No. 18893071.3.

*Primary Examiner* — Alma Pipic
(74) *Attorney, Agent, or Firm* — Sughrue Mion, PLLC

(57) ABSTRACT

The present invention provides a rotigotine-containing patch comprising: a backing layer; and an adhesive agent layer, wherein the adhesive agent layer contains rotigotine and/or a pharmaceutically acceptable salt thereof, the adhesive agent layer further contains a styrene-based thermoplastic elastomer, a petroleum-based resin and/or a terpene-based resin, an aliphatic alcohol, and a cross-linked polyvinylpyrrolidone, and in the adhesive agent layer, a mass ratio of a content of the rotigotine and/or the pharmaceutically acceptable salt thereof in terms of rotigotine free form and a content of the cross-linked polyvinylpyrrolidone (content of the rotigotine and/or the pharmaceutically acceptable salt thereof in terms of rotigotine free form:content of the cross-linked polyvinylpyrrolidone) is 10:3 to 1:3.

7 Claims, 3 Drawing Sheets

(56) References Cited

FOREIGN PATENT DOCUMENTS

| | | |
|---|---|---|
| JP | 2014-177428 A | 9/2014 |
| JP | 2015-503541 A | 2/2015 |
| JP | 2017-515871 A | 6/2017 |
| WO | 2012/084969 A1 | 6/2012 |
| WO | 2013/191158 A1 | 12/2013 |

* cited by examiner

ROTIGOTINE-CONTAINING PATCH

CROSS-REFERENCE TO RELATED APPLICATIONS

This application is a National Stage of International Application No. PCT/JP2018/046137 filed on Dec. 14, 2018, which claims priority under U.S.C. § 119(a) to Japanese Patent Application Nos. JP2017-242845 filed on Dec. 19, 2017 and JP2018-143868 filed on Jul. 31, 2018, the disclosure of which is incorporated herein in its entirety by reference.

TECHNICAL FIELD

The present invention relates to a rotigotine-containing patch, and more particularly to a patch containing rotigotine and/or a pharmaceutically acceptable salt thereof.

BACKGROUND ART

International Application Japanese-Phase Publication No. 2011-504902 (PTL 1) states that rotigotine is the international general name for the compound (−)-5,6,7,8-tetrahydro-6-[propyl-[2-(2-thienyl)ethyl]-amino] 1-naphthalenol, and has crystal polymorphs of type I and type II. Rotigotine is a D1/D2/D3 dopamine receptor agonist, and is mainly used for the treatment of symptoms of Parkinson's disease and restless legs syndrome.

For example, as a formulation for rotigotine administration, "Neupro (registered trademark) Patch" is commercially available in Japan and overseas. In addition, International Application Japanese-Phase Publication No. 2002-509878 (PTL 2) describes a transdermal therapeutic system comprising a backing layer inert to the components of a matrix, a self-adhesive matrix layer containing rotigotine, wherein the matrix is based on a non-aqueous, acrylate-based or silicone-based polymer adhesive having a solubility of 5% (w/w) for rotigotine. Moreover, International Application Japanese-Phase Publication No. 2015-503541 (PTL 3) describes a transdermal therapeutic system comprising a backing layer that is impermeable to active substances, and a matrix layer including a pressure-sensitive adhesive, a drug, and particles of cross-linked polyvinylpyrrolidone, wherein the drug is rotigotine and the pressure-sensitive adhesive is a silicone polymer.

In addition, as a formulation for rotigotine administration using a rubber-based adhesive agent, Japanese Unexamined Patent Application Publication No. 2014-177428 (PTL 4) describes a transdermal absorption-type patch formulation comprising a support, and a drug-containing layer which includes a rubber-based adhesive agent containing a rosin-based resin and a rubber-based adhesive component, and which includes rotigotine or a pharmaceutically acceptable salt thereof, and Japanese Unexamined Patent Application Publication No. 2013-079220 (PTL 5) describes a transdermal absorption-type patch comprising a support, and a drug-containing layer including a rubber-based adhesive agent, rotigotine or a salt thereof, and a production inhibitor of rotigotine decomposition products, for example.

Moreover, as a formulation for rotigotine administration, International Application Japanese-Phase Publication No. 2006-513195 (PTL 6) and International Application Japanese-Phase Publication No. 2012-504609 (PTL 7) state that rotigotine is contained in an amorphous form, and International Application Japanese-Phase Publication No. 2013-515041 (PTL 8) a method for stabilizing rotigotine, comprising the step of providing a solid dispersion containing polyvinylpyrrolidone and amorphous rotigotine using polyvinylpyrrolidone (non-cross-linked) in a specific weight ratio with respect to rotigotine, for example.

In addition, International Application Japanese-Phase Publication No. 2013-510805 (PTL 9) describes a method for preventing the crystallization of a pharmaceutical in a polymer film, comprising drying a solvent-containing coating material applied to produce a polymer film sometimes at a temperature at least 10° C. above the melting temperature of the pharmaceutical present in the coating material. Moreover, International Application Japanese-Phase Publication No. 2017-515871 (PTL 10) describes a method for producing a transdermal absorption formulation obtained by mixing rotigotine and an antioxidant at a specific weight ratio for the purpose of preventing the precipitation of rotigotine crystals.

CITATION LIST

Patent Literature

[PTL 1] International Application Japanese-Phase Publication No. 2011-504902

[PTL 2] International Application Japanese-Phase Publication No. 2002-509878

[PTL 3] International Application Japanese-Phase Publication No. 2015-503541

[PTL 4] Japanese Unexamined Patent Application Publication No. 2014-177428

[PTL 5] Japanese Unexamined Patent Application Publication No. 2013-079220

[PTL 6] International Application Japanese-Phase Publication No. 2006-513195

[PTL 7] International Application Japanese-Phase Publication No. 2012-504609

[PTL 8] International Application Japanese-Phase Publication No. 2013-515041

[PTL 9] International Application Japanese-Phase Publication No. 2013-510805

[PTL 10] International Application Japanese-Phase Publication No. 2017-515871

SUMMARY OF INVENTION

Technical Problem

However, in a rotigotine-containing patch containing rotigotine and/or a pharmaceutically acceptable salt thereof as in the formulations described in PTLs 6 to 8, consider the case where rotigotine is contained in an amorphous form in the presence of rotigotine alone or in the presence of polyvinylpyrrolidone. The amorphous form is in a metastable state in terms of energy, and thus may be transformed with time into a crystal form that is more stable in terms of energy, causing a problem of the precipitation of crystals. Moreover, there is a problem that the production method including specific conditions and steps as described in PTL 9 is complicated and may increase the production cost, failing to achieve sufficient skin permeability of rotigotine even in the case of simply using an antioxidant or the like as described in PTL 10.

In addition, the present inventors made further studies and have found that, even when a rotigotine-containing patch including a backing layer and an adhesive agent layer simply uses a silicone-based adhesive base agent or an acrylic-based adhesive agent which have been conventionally and frequently used in combination with rotigotine, or uses a rubber-based adhesive agent such as polyisobutylene as an adhesive base agent to be contained in the adhesive agent layer, rotigotine and/or a pharmaceutically acceptable salt thereof do not dissolve, or even when temporarily dissolved, crystals derived from rotigotine and/or a pharmaceutically acceptable salt thereof precipitate over time, making it difficult to incorporate rotigotine and/or a pharmaceutically acceptable salt thereof in the adhesive agent layer in a dissolved form. In addition, the present inventors have also found that a mere use of a solubilizer or the like that is conventionally known to have a function of dissolving crystals in order to dissolve such crystals causes a problem that the skin permeability of rotigotine is reduced.

The present invention has been made in view of the above-described problems, and aims to provide a patch containing rotigotine and/or a pharmaceutically acceptable salt thereof in a dissolved form in an adhesive agent layer and having excellent stability over time and skin permeability of rotigotine.

Solution to Problem

The present inventors have made earnest studies to achieve the above object, and have found as a result that it is possible to incorporate rotigotine and/or a pharmaceutically acceptable salt in a complete dissolved form in an adhesive agent layer if, in a patch including a backing layer and an adhesive agent layer, the adhesive agent layer contains at least one selected from the group consisting of rotigotine and pharmaceutically acceptable salts thereof (hereinafter sometimes referred to as "rotigotine and/or a pharmaceutically acceptable salt thereof"), a styrene-based thermoplastic elastomer, at least one selected from the group consisting of petroleum-based resins and terpene-based resins (hereinafter sometimes referred to as "a petroleum-based resin and/or a terpene-based resin"), an aliphatic alcohol, and cross-linked polyvinylpyrrolidone, and further, the blending ratio (mass ratio) of rotigotine and/or a pharmaceutically acceptable salt thereof and cross-linked polyvinylpyrrolidone is within a specific range.

The present inventors have also found that the rotigotine-containing patch having such a constitution achieves a high level of rotigotine skin permeability, and moreover that even when a long period of time has passed since the production, crystals of rotigotine and/or a pharmaceutically acceptable salt thereof are not precipitated, so that the above-described excellent skin permeability and formulation properties are maintained, and stability over time is exhibited. Thus, the present invention has been completed.

Specifically, the rotigotine-containing patch of the present invention is a rotigotine-containing patch comprising: a backing layer; and an adhesive agent layer, wherein the adhesive agent layer contains rotigotine and/or a pharmaceutically acceptable salt thereof, the adhesive agent layer further contains a styrene-based thermoplastic elastomer, a petroleum-based resin and/or a terpene-based resin, an aliphatic alcohol, and a cross-linked polyvinylpyrrolidone, and in the adhesive agent layer, a mass ratio of a content of the rotigotine and/or the pharmaceutically acceptable salt thereof in terms of rotigotine free form and a content of the cross-linked polyvinylpyrrolidone (content of the rotigotine and/or the pharmaceutically acceptable salt thereof in terms of rotigotine free form:content of the cross-linked polyvinylpyrrolidone) is 10:3 to 1:3.

In the rotigotine-containing patch of the present invention, preferably, the adhesive agent layer contains the rotigotine and/or the pharmaceutically acceptable salt thereof in a dissolved form. In addition, preferably, the aliphatic alcohol has 12 to 23 carbon atoms.

Moreover, in the rotigotine-containing patch of the present invention, the content of the rotigotine and/or the pharmaceutically acceptable salt thereof in the adhesive agent layer in terms of rotigotine free form is preferably 5 to 15% by mass relative to a total mass of the adhesive agent layer, a content of the petroleum-based resin and/or the terpene-based resin in the adhesive agent layer is preferably 5 to 80% by mass relative to the total mass of the adhesive agent layer, and a content of the aliphatic alcohol in the adhesive agent layer is preferably 1 to 15% by mass relative to the total mass of the adhesive agent layer.

In addition, in the rotigotine-containing patch of the present invention, preferably, the adhesive agent layer further contains a stabilizer.

Note that, in the present invention, the "dissolved form" of a drug means that the drug is molecularly diffused in the adhesive agent layer at room temperature (25° C.). The dissolved form of a drug can be confirmed by the absence of an endothermic melting point peak derived from crystals and a baseline shift due to a glass transition derived from an amorphous substance in differential scanning calorimetry (DSC). When the drug is a rotigotine free form, the endothermic melting point peak (melting point) can be determined from a peak observed in a thermogram obtained by heating crystals of a drug from 10° C. to 120° C. at a rate of temperature rise of 10° C./min and performing DSC measurement using a differential scanning calorimeter. For example, as shown in FIGS. 1 and 2, an endothermic melting point peak is observed at around 78° C. (FIG. 1) when the free form crystals of rotigotine are of type I, and at around 97° C. (FIG. 2) when the free form crystals of rotigotine are of type II. Moreover, the baseline shift due to a glass transition can be determined from a baseline shift observed in a thermogram obtained by heating an amorphous drug from 10° C. to 120° C. at a rate of temperature rise of 10° C./min and performing DSC measurement using a differential scanning calorimeter. In addition, for example, when the drug is rotigotine hydrochloride, the endothermic melting point peak and the baseline shift due to a glass transition can be determined from a peak observed in a thermogram obtained by performing DSC measurement in the same manner as described above except that the heating temperature is from 10° C. to 190° C.

Advantageous Effects of Invention

The present invention makes it possible to provide a rotigotine-containing patch containing rotigotine and/or a pharmaceutically acceptable salt thereof in a dissolved form in an adhesive agent layer and having excellent stability over time and skin permeability of rotigotine.

DESCRIPTION OF EMBODIMENTS

Figure 1:
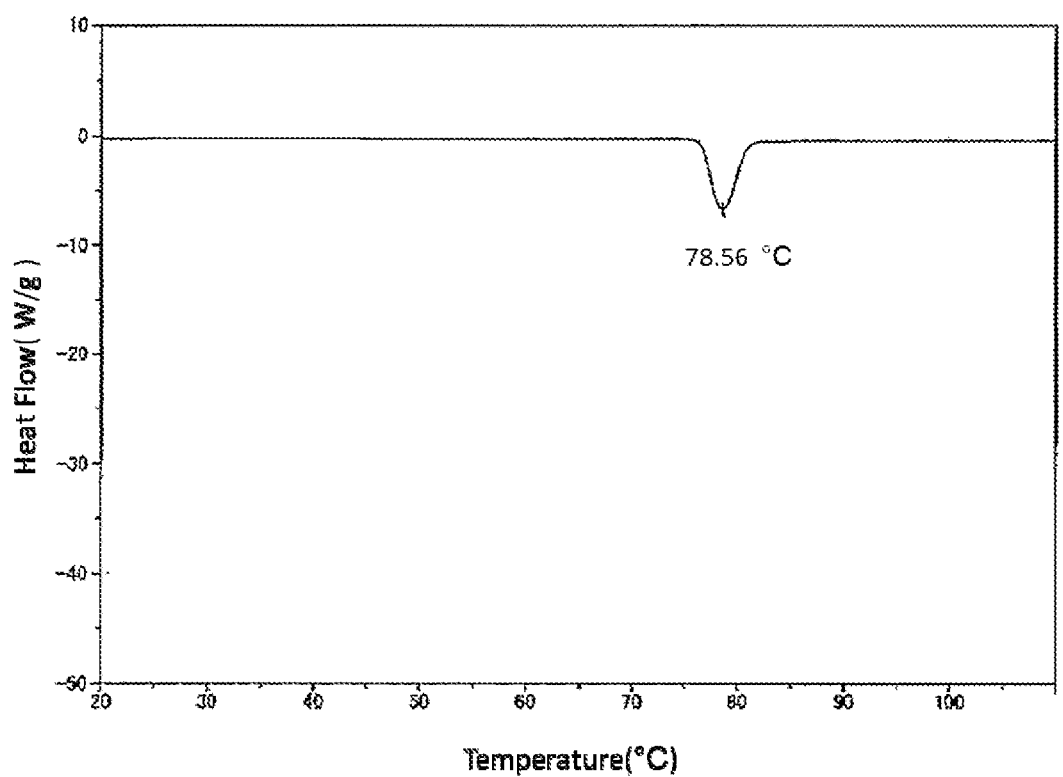
FIG. 1 is a graph showing the results of performing a DSC measurement of type I crystals of rotigotine free form.

Hereinafter, the present invention is described in detail with reference to preferred embodiments. The rotigotine-containing patch of the present invention is a patch comprising: a backing layer; and an adhesive agent layer, wherein the adhesive agent layer contains rotigotine and/or a pharmaceutically acceptable salt thereof, the adhesive agent layer further contains a styrene-based thermoplastic elastomer, a petroleum-based resin and/or a terpene-based resin, an aliphatic alcohol, and a cross-linked polyvinylpyrrolidone, and in the adhesive agent layer, a mass ratio of a content of the rotigotine and/or the pharmaceutically acceptable salt thereof in terms of rotigotine free form and a content of the cross-linked polyvinylpyrrolidone (content of the rotigotine and/or the pharmaceutically acceptable salt thereof in terms of rotigotine free form:content of the cross-linked polyvinylpyrrolidone) is 10:3 to 1:3.

The rotigotine-containing patch of the present invention includes a backing layer and an adhesive agent layer. The backing layer is not particularly limited as long as it can support the adhesive agent layer to be described later, and a known backing layer for a patch can be appropriately employed. Examples of the material of the backing layer according to the present invention include polyolefins such as polyethylene and polypropylene; ethylene-vinyl acetate copolymer, vinyl acetate-vinyl chloride copolymer, polyvinyl chloride, and the like; polyamides such as nylon; polyesters such as polyethylene terephthalate (PET), polybutylene terephthalate, and polyethylene naphthalate; cellulose derivatives; and synthetic resins such as polyurethane, and metals such as aluminum. Among these, polyesters and polyethylene terephthalate are preferable from the viewpoint of non-adsorbability and non-permeability of drugs. Examples of the form of the backing layer include films; sheet-shaped objects such as sheets, sheet-shaped porous bodies, and sheet-shaped foams; fabrics such as woven fabrics, knitted fabrics, and nonwoven fabrics; foils; and laminates thereof. In addition, the thickness of the backing layer is not particularly limited, but is preferably in the range of 5 to 1000 pm from the viewpoints of workability and ease of production when applying the patch.

The rotigotine-containing patch of the present invention may further include a release liner on the surface of the adhesive agent layer opposite to the backing layer. Examples of such release liner include polyolefins such as polyethylene and polypropylene; ethylene-vinyl acetate copolymer, vinyl acetate-vinyl chloride copolymer, polyvinyl chloride, and the like; polyamides such as nylon; polyesters such as polyethylene terephthalate; cellulose derivatives; and films and sheets made of materials such as synthetic resins including polyurethane, aluminum, and paper, and laminates thereof. Preferably, these release liners have been subjected to a release treatment using a silicone-containing compound coat, a fluorine-containing compound coat, or the like on the surface in contact with the adhesive agent layer so as to easily enable release from the adhesive agent layer.

<Rotigotine and Pharmaceutically Acceptable Salt Thereof>

The adhesive agent layer according to the present invention contains at least one selected from the group consisting of rotigotine and pharmaceutically acceptable salts thereof as a drug. In the present invention, the form of rotigotine contained in the adhesive agent layer may be a free form or a pharmaceutically acceptable salt thereof, may be a pharmaceutically acceptable salt of rotigotine that has been desalted into a free form in the formulation during production and/or after production, or may be one of these or a mixture of two or more thereof. Examples of the pharmaceutically acceptable salt of rotigotine include acid addition salts, and examples of the acid addition salts include hydrochloric acid, sulfuric acid, nitric acid, phosphoric acid, phosphorous acid, hydrobromic acid, maleic acid, malic acid, ascorbic acid, tartaric acid, lauric acid, stearic acid, palmitic acid, oleic acid, myristic acid, lauryl sulfate, linolenic acid, and fumaric acid. Among these, the adhesive agent layer according to the present invention preferably contains rotigotine in a free form.

In the present invention, the content of rotigotine and/or a pharmaceutically acceptable salt thereof contained in the adhesive agent layer (the content of rotigotine, the content of a pharmaceutically acceptable salt of rotigotine, or the total content thereof if both of them are contained, hereinafter the same) is, in terms of rotigotine free form, preferably 5 to 15% by mass, more preferably 7 to 12% by mass, and further preferably 8 to 10% by mass relative to the total mass of the adhesive agent layer. When the content of rotigotine and/or a pharmaceutically acceptable salt thereof is less than the lower limit, the skin permeability of rotigotine tends to decrease. Meanwhile, when the upper limit is exceeded, there is a tendency that crystals of rotigotine and/or a pharmaceutically acceptable salt thereof are precipitated, an amorphous type is formed, and the adhesive force of the adhesive agent layer is easily reduced.

<Styrene-Based Thermoplastic Elastomer>

The adhesive agent layer according to the present invention contains a styrene-based thermoplastic elastomer as an adhesive base agent. Particularly when a styrene-based thermoplastic elastomer is contained in the adhesive agent layer in the constitution of the present invention, it is possible to incorporate rotigotine and/or a pharmaceutically acceptable salt thereof more stably in the adhesive agent layer in a dissolved form.

The styrene-based thermoplastic elastomer according to the present invention is a thermoplasticity-exhibiting styrene-based elastomer which exhibits fluidity by softening when heated, and which returns to a rubber-like elastic body when cooled. Among these, a styrene-based block copolymer is preferred from the viewpoint of sufficient tackiness impartment and stability over time.

Specific examples of the styrene-based block copolymer include styrene-butadiene block copolymer, styrene-butadiene-styrene block copolymer (SBS), styrene-isoprene block copolymer, styrene-isoprene-styrene block copolymer (SIS), styrene-ethylene/butylene block copolymer, styrene-ethylene/butylene-styrene block copolymer, styrene-ethylene/propylene block copolymer, styrene-ethylene/propylene-styrene block copolymer, styrene-isobutylene block copolymer, and styrene-isobutylene-styrene block copolymer, and one of these may be used alone, or two or more may be used in combination. Note that, in the above, "ethylene/butylene" indicates a copolymer block of ethylene and butylene, and "ethylene/propylene" indicates a copolymer block of ethylene and propylene. Among these, the styrene-based thermoplastic elastomer according to the present invention is more preferably a styrene-isoprene-styrene block copolymer.

The styrene-isoprene-styrene block copolymer has a viscosity average molecular weight of preferably 30,000 to 2,500,000, and more preferably 100,000 to 1,700,000. When the viscosity average molecular weight is less than the lower limit, the formulation properties of the patch (particularly the cohesive force of the adhesive agent layer) tend to decrease. Meanwhile, when the upper limit is exceeded, there is a tendency that the compatibility with other components contained in the adhesive agent layer is reduced, making it difficult to produce a patch.

In the present invention, the content of the styrene-based thermoplastic elastomer contained in the adhesive agent layer is preferably 5 to 50% by mass, more preferably 10 to 40% by mass, and further preferably 10 to 30% by mass relative to the total mass of the adhesive agent layer. When the content of the styrene-based thermoplastic elastomer is less than the lower limit, the cohesive force, shape retainability, and the like of the adhesive agent layer tend to decrease. Meanwhile, when the upper limit is exceeded, there is a tendency that the cohesive force of the adhesive agent layer excessively increases, so that the adhesive force of the adhesive agent layer decreases or the compatibility decreases.

<Petroleum-Based Resin.Terpene-Based Resin>

The adhesive agent layer according to the present invention further contains at least one selected from the group consisting of petroleum-based resins and terpene-based resins. In the present invention, when the petroleum-based resin and/or the terpene-based resin is contained, a high level of skin permeability is achieved, and moreover, the production of rotigotine analog substances is further suppressed, and the stability over time is further improved.

(Petroleum-Based Resin)

Examples of the petroleum-based resin according to the present invention include C5-based synthetic petroleum resins (such as copolymer of at least two of isoprene, cyclopentadiene, 1,3-pentadiene, and 1-pentene; copolymer of at least two of 2-pentene and dicyclopentadiene; and 1,3-pentadiene-based resin), C9-based synthetic petroleum resins (such as copolymer of at least two of indene, styrene, methylindene, and α-methylstyrene), and dicyclopentadiene-based synthetic petroleum resin (copolymer with isoprene and/or 1,3-pentadiene mainly composed of dicyclopentadiene). In addition, from the viewpoint of another classification, examples include alicyclic petroleum resins (such as alicyclic saturated hydrocarbon resins), alicyclic hydrogenated petroleum resins, aliphatic petroleum resins (such as aliphatic hydrocarbon resins), aliphatic hydrogenated petroleum resins, and aromatic petroleum resins, and more specific examples include Arkon P-70, Arkon P-85, Arkon P-90, Arkon P-100, Arkon P-115, Arkon P-125 (these are trade names, manufactured by Arakawa Chemical Industries, Ltd.), and Escorez 8000 (trade name, manufactured by Esso). As the petroleum-based resin according to the present invention, one of these may be used alone, or two or more may be used in combination. Among these, an alicyclic saturated hydrocarbon resin is more preferable from the viewpoint that suitable adhesion to the skin is easily obtained, the feeling of use is good due to little odor and the like, and the production of rotigotine analog substances is further suppressed.

In the present invention, the alicyclic saturated hydrocarbon resin refers to a resin that is a homopolymer or copolymer of alicyclic saturated hydrocarbon monomers. The alicyclic saturated hydrocarbon resin has a weight average molecular weight of preferably 1,000 to 1,500, and more preferably 1,200 to 1,400.

(Terpene-Based Resin)

Examples of the terpene-based resin according to the present invention include pinene polymers (such as α-pinene polymers and β-pinene polymers), terpene polymers, dipentene polymers, terpene-phenol polymers, aromatic modified terpene polymers, and pinene-phenol copolymers. More specific examples include YS RESIN (such as YS RESIN PXN (1150N, 300N), YS RESIN PX1000, YS RESIN TO125, and YS RESIN TO105), CLEARON P105, CLEARON M115, CLEARON K100 (these are trade names, manufactured by YASUHARA CHEMICAL CO., LTD.), and Tamanol 901 (trade name, manufactured by Arakawa Chemical Industries, Ltd.), and one of these may be used alone, or two or more may be used in combination. Among these, the terpene-based resin according to the present invention is more preferably a pinene polymer from the viewpoint that suitable adhesion to the skin is easily obtained, and the feeling of use is good due to little odor and the like.

In the present invention, the content of the petroleum-based resin and/or the terpene-based resin contained in the adhesive agent layer (the content of petroleum-based resin or the terpene-based resin, or the total content thereof if both of them are contained, hereinafter the same) is preferably 5 to 80% by mass, more preferably 10 to 70% by mass, further preferably 10 to 60% by mass, and particularly preferably 20 to 60% by mass relative to the total mass of the adhesive agent layer. When the content of the petroleum-based resin and/or the terpene-based resin is less than the lower limit, there is a tendency that the adhesive force of the adhesive agent layer and the adhesion to the skin decrease, and the effect of suppressing the production of rotigotine analog substances is not insufficiently exhibited. Meanwhile, when the upper limit is exceeded, the transdermal absorbability of the drug and the shape retainability of the adhesive agent layer tend to decrease.

<Aliphatic Alcohol>

The adhesive agent layer according to the present invention further contains an aliphatic alcohol. In the present invention, the aliphatic alcohol refers to a saturated or unsaturated, linear or branched, monohydric or dihydric or higher aliphatic alcohol.

The aliphatic alcohol according to the present invention is preferably monohydric. In addition, the number of carbon atoms of the aliphatic alcohol according to the present invention is preferably 3 to 23 carbon atoms and more preferably 12 to 23 carbon atoms, further preferably 17 to 23 and particularly preferably 19 to 21 from the viewpoint of stability over time, and particularly preferably 12 to 20 from the viewpoint of skin permeability. When the number of carbon atoms of the aliphatic alcohol is less than the lower limit, the boiling point is low and thus it is difficult to keep a constant content in the formulation, so that the stability over time tends to decrease. Meanwhile, when the upper limit is exceeded, the compatibility with the adhesive base agent and other components tends to decrease.

Examples of the aliphatic alcohol according to the present invention include isopropanol, hexyl alcohol, lauryl alcohol, myristyl alcohol, cetyl alcohol, stearyl alcohol, isostearyl alcohol, octyldodecanol, oleyl alcohol, linolenyl alcohol, and hexyldecanol, and one of these may be used alone, or two or more may be used in combination. Among these, the aliphatic alcohol according to the present invention is particularly preferably at least one selected from the group consisting of octyldodecanol and lauryl alcohol from the viewpoint that the skin permeability of rotigotine tends to be particularly improved, in addition to the viewpoints of stability over time and compatibility described above.

In the present invention, the content of the aliphatic alcohol contained in the adhesive agent layer is, in the case of two or more kinds, preferably 1 to 15% by mass, more preferably 1 to 10% by mass, further preferably 2 to 7% by mass, and particularly preferably 3 to 7% by mass in total relative to the total mass of the adhesive agent layer. When the content of the aliphatic alcohol is less than the lower limit, the skin permeability of rotigotine tends to decrease. Meanwhile, when the upper limit is exceeded, the compatibility with the adhesive base agent and other components tends to decrease.

<Cross-Linked Polyvinylpyrrolidone>

The adhesive agent layer according to the present invention further contains cross-linked polyvinylpyrrolidone (also referred to as "cross-linked PVP" or "crospovidone").

Examples of the cross-linked polyvinylpyrrolidone according to the present invention include a cross-linked N-vinylpyrrolidone polymer. The N-vinylpyrrolidone polymer may be a homopolymer or a copolymer, and examples thereof include a homopolymer of N-vinylpyrrolidone and a copolymer of N-vinylpyrrolidone and a polyfunctional monomer. Among these, the cross-linked polyvinylpyrrolidone according to the present invention is preferably a cross-linked homopolymer of 1-vinyl-2-pyrrolidone (also referred to as "crospovidone"). As crospovidone, commercially available ones may be used, such as Kollidon CL and Kollidon CL-M (manufactured by BASF Japan); and Polyplasdone XL, Polyplasdone XL-10, and Polyplasdone INF-10 (manufactured by ISP Japan).

In the present invention, the content of the cross-linked polyvinylpyrrolidone contained in the adhesive agent layer needs to be 10:3 to 1:3 in a mass ratio with the content of the rotigotine and/or the pharmaceutically acceptable salt thereof (content of the rotigotine and/or the pharmaceutically acceptable salt thereof in terms of rotigotine free form:content of the cross-linked polyvinylpyrrolidone). When the content of the cross-linked polyvinylpyrrolidone relative to the rotigotine and/or the pharmaceutically acceptable salt thereof is less than the lower limit, crystals of the rotigotine and/or the pharmaceutically acceptable salt thereof precipitate. Meanwhile, when the upper limit is exceeded, it becomes difficult to achieve excellent skin permeability of rotigotine. The mass ratio (content of the rotigotine and/or the pharmaceutically acceptable salt thereof in terms of rotigotine free form:content of the cross-linked polyvinylpyrrolidone) is preferably 10:3 to 1:2.5, and more preferably 10:3 to 1:2 from the viewpoint that the stability over time and the skin permeability of rotigotine tend to be superior.

In addition, the content of the cross-linked polyvinylpyrrolidone contained in the adhesive agent layer is preferably 3 to 25% by mass, more preferably 3 to 20% by mass, and further preferably 3 to 15% by mass relative to the total mass of the adhesive agent layer. When the content of the cross-linked polyvinylpyrrolidone is less than the lower limit, crystals of rotigotine and/or a pharmaceutically acceptable salt thereof tend to easily precipitate. Meanwhile, if the upper limit is exceeded, there is a tendency that the compatibility of the adhesive agent layer composition at the time of production decreases, making the production difficult.

<Additional Components>

As long as the effects of the present invention are not impaired, the adhesive agent layer according to the present invention may further contain additives such as additional drugs other than rotigotine and a pharmaceutically acceptable salt thereof; additional adhesive base agents other than the styrene-based thermoplastic elastomer; tackifiers; absorption enhancers; adsorbents, desalting agents, plasticizers, solubilizers, fillers, stabilizers, and preservatives.

(Additional Drugs)

Examples of the additional drugs other than rotigotine and the pharmaceutically acceptable salt thereof include non-steroidal anti-inflammatory analgesics (such as diclofenac, indomethacin, ketoprofen, felbinac, loxoprofen, ibuprofen, flurbiprofen, tiaprofen, acemetacin, sulindac, etodolac, tolmetin, piroxicam, meloxicam, ampiroxicam, naproxen, azapropazone, methyl salicylate, glycol salicylate, valdecoxib, celecoxib, rofecoxib, and amfenac), antipyretic analgesics (such as acetaminophen), antihistamines (such as diphenhydramine, chlorpheniramine, mequitazine, and homochlorcyclizine), antihypertensives (such as diltiazem, nicardipine, nilvadipine, metoprolol, bisoprolol, and trandolapril), antiparkinsonian drugs (such as pergolide, ropinirole, bromocriptine, and selegiline), bronchodilators (such as tulobuterol, isoproterenol, and salbutamol), antiallergic agents (such as ketotifen, loratadine, azelastine, terfenadine, cetirizine, and acitazanolast), local anesthetics (such as lidocaine and dibucaine), neuropathic pain medications (such as pregabalin), non-narcotic analgesics (buprenorphine, tramadol, pentazocine), anesthetic analgesics (such as morphine, oxycodone, and fentanyl), agents for urinary organs (such as oxybutynin and tamsulosin), psychotropic agents (such as promazine and chlorpromazine), steroid hormones (such as estradiol, progesterone, norethisterone, cortisone, and hydrocortisone), antidepressants (such as sertraline, fluoxetine, paroxetine, and citalopram), anti-dementia drugs (such as donepezil, rivastigmine, and galantamine), antipsychotics (such as risperidone and olanzapine), central nervous system stimulants (such as methylphenidate), osteoporosis medications (such as raloxifene and alendronate), breast cancer prevention drugs (such as tamoxifen), anti-obesity drugs (such as mazindol and sibutramine), insomnia improving drugs (such as melatonin), and antirheumatic drugs (such as actarit), and one of these may be used alone, or two or more may be used in combination.

In the present invention, consider the case where these additional drugs are further contained in the adhesive agent layer. The content thereof is, in the case of two or more kinds, preferably 10% by mass or less in total relative to the total mass of the adhesive agent layer.

(Additional Adhesive Base Agent)

Examples of the additional adhesive base agents other than the styrene-based thermoplastic elastomer include rubber-based adhesive base agents other than the styrene-based thermoplastic elastomer, acrylic-based adhesive base agents, and silicone-based adhesive base agents, and one of these may be used alone, or two or more may be used in combination.

Examples of the rubber-based adhesive base agents other than the styrene-based thermoplastic elastomer include isoprene rubber, polyisobutylene (PIB), and polybutene, and one of these may be used alone, or two or more may be used in combination. Among these, it is preferable to use polyisobutylene from the viewpoint that the tackiness and cohesive force of the adhesive agent layer tend to be further improved. In that case, it is more preferable that the mass ratio of the styrene-based thermoplastic elastomer (more preferably styrene-isoprene-styrene block copolymer) to the polyisobutylene (mass of the styrene-based thermoplastic elastomer:mass of PIB) be 1:2 to 30:1 (further preferably within the range of 1:1 to 10:1).

Examples of the acrylic-based adhesive base agents are listed in "Japanese Pharmaceutical Excipients Directory 2016 (edited by International Pharmaceutical Excipients Council Japan)" as adhesive agents, such as acrylic acid.octyl acrylate ester copolymer, 2-ethylhexyl acrylate.vinyl pyrrolidone copolymer, acrylate ester.vinyl acetate copolymer, 2-ethylhexyl acrylate.2-ethylhexyl methacrylate.dodecyl methacrylate copolymer, methyl acrylate.2-ethylhexyl acrylate copolymer resin, 2-ethylhexyl acrylate.methyl acrylate.acrylic acid.glycidyl methacrylate copolymer, 2-ethylhexyl acrylate.vinyl acetate.hydroxyethyl acrylate.glycidyl methacrylate copolymer, 2-ethylhexyl acrylate.diacetone acrylamide.acetoacetoxyethyl methacrylate.methyl methacrylate copolymer, ethyl acrylate.methyl methacrylate copolymer, acrylic-based polymer contained in an alkanolamine solution of acrylic resin, and one of these may be used alone, or two or more may be used in combination.

Examples of the silicone-based adhesive base agents include polydimethylsiloxane (such as the polymer represented by MQ in the representation by ASTM D-1418), polymethylvinylsiloxane (such as the polymer represented by VMQ in the representation by ASTM D-1418), and polymethylphenylsiloxane (such as the polymer represented by PVMQ in the representation by ASTM D-1418), and one of these may be used alone, or two or more may be used in combination.

In the present invention, consider the case where these additional adhesive base agents are further contained. The content thereof is, in the case of two or more kinds, preferably 10% by mass or less in total relative to the total mass of the adhesive agent layer.

(Tackifier)

The tackifier is blended mainly for the purpose of increasing the tackiness of the adhesive base agent. Examples of the tackifier include tackifier resins other than the petroleum-based resin and terpene-based resin, such as rosin-based resins, phenol-based resins, and xylene-based resins, and one of these may be used alone, or two or more may be used in combination. In the present invention, consider the case where these tackifiers are further contained. The content thereof is, in the case of two or more kinds, preferably 10% by mass or less in total relative to the total mass of the adhesive agent layer.

(Absorption Enhancer (Transdermal Absorption Enhancer))

Examples of the absorption enhancers include those having an effect of promoting the transdermal absorption of drugs other than the aliphatic alcohol, such as fatty acids having 6 to 20 carbon atoms, fatty acid esters, fatty acid amides, or aliphatic alcohol ethers; aromatic organic acids; aromatic alcohols; aromatic organic acid esters or ethers; POE hydrogenated castor oils; lecithins; phospholipids; soybean oil derivatives; and triacetin, and one of these may be used alone, or two or more may be used in combination. In the present invention, consider the case where these absorption enhancers are further contained. The content thereof is, in the case of two or more kinds, preferably 10% by mass or less in total relative to the total mass of the adhesive agent layer.

(Additive)

[Adsorbent]

Examples of the adsorbents include hygroscopic inorganic and/or organic substances, and more specific examples thereof include minerals such as talc, kaolin, and bentonite; silicon compounds such as fumed silica (such as AEROSIL (registered trademark)) and hydrous silica; metal compounds such as zinc oxide and dried aluminum hydroxide gel; weak acids such as lactic acid and acetic acid; sugars such as dextrin; and polymers such as polyvinylpyrrolidone (non-cross-linked PVP), aminoalkyl methacrylate copolymer, carboxyvinyl polymer, and butyl methacrylate methyl methacrylate copolymer, and one of these may be used alone, or two or more may be used in combination. In the present invention, consider the case where these adsorbents are further contained in the adhesive agent layer. The content thereof is, in the case of two or more kinds, preferably 10% by mass or less in total relative to the total mass of the adhesive agent layer.

[Desalting Agent]

The desalting agent is blended mainly for the purpose of converting all or a part of the basic drug into a free form. Such a desalting agent is not particularly limited, but is preferably, for example, a basic substance, and more preferably a metal ion-containing desalting agent or a basic nitrogen atom-containing desalting agent in the case of blending an acid addition salt of drug as the drug to obtain a formulation containing a free form drug. Examples of the metal ion-containing desalting agent include sodium acetate (including anhydrous sodium acetate), sodium hydroxide, potassium hydroxide, magnesium hydroxide, sodium hydrogen carbonate, potassium hydrogen carbonate, sodium citrate, and sodium lactate, and one of these may be used alone, or two or more may be used in combination. Note that the adhesive agent layer according to the present invention may further contain a compound derived from the basic drug and the desalting agent (for example, when rotigotine hydrochloride and sodium acetate are combined, sodium hydrochloride). In the present invention, consider the case where these desalting agents and compounds derived from basic drugs and desalting agents are further contained in the adhesive agent layer. The content thereof is, in the case of two or more kinds, preferably 10% by mass or less in total relative to the total mass of the adhesive agent layer.

[Plasticizer]

The plasticizer is blended mainly for the purpose of adjusting the adhesive properties of the adhesive agent layer, flow characteristics in the production of the adhesive agent layer, transdermal absorption characteristics of the drug, and the like. Examples of such a plasticizer include silicone oils; petroleum-based oils such as paraffinic process oils, naphthenic process oils, and aromatic process oils; squalane, squalene; vegetable-based oils such as olive oil, camellia oil, castor oil, tall oil, and peanut oil; dibasic acid esters such as dibutyl phthalate and dioctyl phthalate; liquid rubbers such as polybutene and liquid isoprene rubber; and diethylene glycol, polyethylene glycol, propylene glycol, and dipropylene glycol, and one of these may be used alone, or two or more may be used in combination. Among these, silicone oil, liquid paraffin, and liquid polybutene are preferable as the plasticizer. In the present invention, consider the case where plasticizers are further contained in the adhesive agent layer. The content thereof is, in the case of two or more kinds, preferably 5 to 30% by mass, and more preferably 10 to 20% by mass in total relative to the total mass of the adhesive agent layer, from the viewpoint of improving the adhesive force of the adhesive agent layer and/or alleviating local irritation during release.

[Solubilizer.Filler]

Examples of the solubilizers include organic acids such as acetic acid, and surfactants, and one of these may be used alone, or two or more may be used in combination. In addition, the filler is blended mainly for the purpose of adjusting the adhesive force of the adhesive agent layer, and examples of the filler include aluminum hydroxide, calcium carbonate, and magnesium carbonate; silicates such as aluminum silicate and magnesium silicate; and silicic acid, barium sulfate, calcium sulfate, calcium zincate, zinc oxide, and titanium oxide, and one of these may be used alone, or two or more may be used in combination.

[Stabilizer]

Examples of the stabilizers include ascorbic acid, metal salts, or esters thereof (preferably sodium salts and palmitate esters), isoascorbic acid or metal salts thereof (preferably sodium salts), ethylenediaminetetraacetic acid or metal salts thereof (preferably calcium disodium salts and tetrasodium salts), cysteine, acetylcysteine, 2-mercaptobenzimidazole, dibutylhydroxytoluene, butylhydroxyanisole, propyl gallate, pentaerythrityl-tetrakis[3-(3,5-di-t-butyl-4-hydroxyphenyl) propionate], 3-mercapto-1,2-propanediol, tocopherol acetate, thymol, soy lecithin, rutin, dihydroxybenzoic acid, potassium dichloroisocyanurate, quercetin, hydroquinone, metal salts of hydroxymethanesulfinic acid (preferably sodium salts), metal metabisulfites (such as sodium salts), metal sulfites (preferably sodium salts), and metal thiosulfates (preferably sodium salt), and one of these may be used alone, or two or more may be used in combination. In the above, examples of the metal salts include sodium salts, potassium salts, calcium salts, and magnesium salts. In addition, examples of the esters include palmitate esters, stearate esters, and myristate esters.

In the present invention, preferably, the adhesive agent layer further contains the stabilizer from the viewpoint that the stability over time tends to be further improved. In this case, the content of the stabilizer is, in the case of two or more kinds, preferably 0.001 to 5% by mass, more preferably 0.005 to 3% by mass, and further preferably 0.01 to 2% by mass in total relative to the total mass of the adhesive agent layer. When the content of the stabilizer exceeds the upper limit, the properties of the adhesive agent layer such as adhesiveness may be reduced. Meanwhile, when the lower limit is fallen short of, the stabilizing effect of the stabilizer tends to be insufficient.

[Preservative]

Examples of the preservatives include derivatives of paraoxybenzoic acid, benzyl alcohol, phenol, and cresol, and one of these may be used alone, or two or more may be used in combination.

Consider the case where the above additives are further contained in the adhesive agent layer. The content thereof is, in the case of two or more kinds, preferably 40% by mass or less, and more preferably 30% by mass or less in total relative to the total mass of the adhesive agent layer.

The adhesive agent layer according to the present invention is not particularly limited, but has a mass per unit area (area of the sticking surface) of preferably 20 to 200 $g/m^2$, more preferably 30 to 100 $g/m^2$, and further preferably 30 to 70 $g/m^2$. In addition, the area of the sticking surface of the adhesive agent layer according to the present invention can be appropriately adjusted depending on the purpose of treatment and the target of application, and is not particularly limited, but is usually in the range of 0.5 to 200 $cm^2$.

The rotigotine-containing patch of the present invention is not particularly limited, and can be produced by appropriately employing a known patch production method. For example, first, rotigotine and/or a pharmaceutically acceptable salt thereof, the styrene-based thermoplastic elastomer, the petroleum-based resin and/or the terpene-based resin, the aliphatic alcohol, the cross-linked polyvinylpyrrolidone, and optionally a solvent and the additional components are kneaded in a usual manner to obtain a uniform adhesive agent layer composition. In the case of using a rotigotine free form as the rotigotine and/or the pharmaceutically acceptable salt thereof, the I-type crystals, II-type crystals, or amorphous form thereof may be used, or a mixture of at least two or more of the I-type crystals, II-type crystals, and amorphous form may be used. In addition, as the rotigotine and/or the pharmaceutically acceptable salt thereof, those dissolved in the solvent may be used. Examples of the solvent include anhydrous ethanol, toluene, heptane, methanol, ethyl acetate, hexane, and a mixture of at least two or more of these.

Next, this adhesive agent layer composition is applied onto the surface (usually onto one surface) of the backing layer to a desired mass per unit area, and then the solvent is dried and removed by heating as necessary to form an adhesive agent layer, which is further cut into a desired shape as necessary. Thereby, it is possible to obtain the patch of the present invention.

In addition, the method for producing a rotigotine-containing patch of the present invention may further include a step of attaching the release liner to the surface of the adhesive agent layer opposite to the backing layer, the step including first applying the adhesive agent layer composition onto one surface of the release liner to a desired mass per unit area to form an adhesive agent layer, then attaching the backing layer to the surface of the adhesive agent layer opposite to the release liner, and cutting the unit into a desired shape as necessary, thereby obtaining the patch of the present invention. Moreover, the obtained patch may be enclosed in a preservation packaging container (such as an aluminum laminate bag) as necessary to form a package.

EXAMPLES

Hereinafter, the present invention is described more specifically based on Examples and Comparative Examples, but the present invention is not limited to the following Examples. Note that, in each of Examples and Comparative Examples, the skin permeation test, the crystal precipitation evaluation, and the differential scanning calorimetry were performed by the following methods.

<Skin Penetration Test (In Vitro Hairless Mouse Skin Penetration Test)>

First, to the stratum corneum side of a fat-removed skin piece obtained by peeling the skin of the hairless mouse body to remove fat, a patch cut into a square of 1.0 $cm^2$ with the release liner removed was attached. In this way, a test sample was prepared. This was set in a flow-through type diffusion cell such that the dermis side was in contact with receptor solution, and the cell was filled with a receptor solution (phosphate buffered saline). Next, the receptor solution was sent at a flow rate of about 5 mL/hr while circulating warm circulating water around the outer periphery so that the receptor solution was kept at 32° C., and the receptor solution was collected every two hours up to 24 hours. The rotigotine concentration in the collected receptor solution was measured by high performance liquid chromatography, and the following formula:

amount of skin permeation of rotigotine ($\mu g/cm^2$)={rotigotine concentration in receptor solution ($\mu g/mL$)×flow rate (mL)}/area of patch ($cm^2$)

was used calculate the rate of skin permeation of rotigotine per unit area of the adhesive agent layer, thereby obtaining the rate of skin permeation per hour (rate of skin permeation ($\mu g/cm^2/hr$)). Each measurement was performed on two test samples, and the average of the maximum values of rate of skin permeation within 24 hours was defined as the maximum rate of skin permeation (Jmax).

<Crystal Precipitation Evaluation>

The patch obtained in each of Examples and Comparative Examples was enclosed in an aluminum laminate bag to prepare a test sample, which was stored at room temperature (about 25° C.) for 3 days or 6 months, and the surface of the adhesive agent layer after storage was observed visually and with an optical microscope. The crystal precipitation condition and the presence or absence of amorphous particles on the surface of each adhesive agent layer were evaluated based on the following criteria:

A: neither crystalline particles nor amorphous particles are observed visually and with an optical microscope, and B: crystalline particles and/or amorphous particles are observed visually or with an optical microscope.

Each evaluation was performed on two test samples, but there was no difference between the two test samples obtained in each of the following Examples and Comparative Examples, and the evaluation results were as shown in the following tables.

<Differential Scanning Calorimetry (DSC Measurement)>

Figure 2:
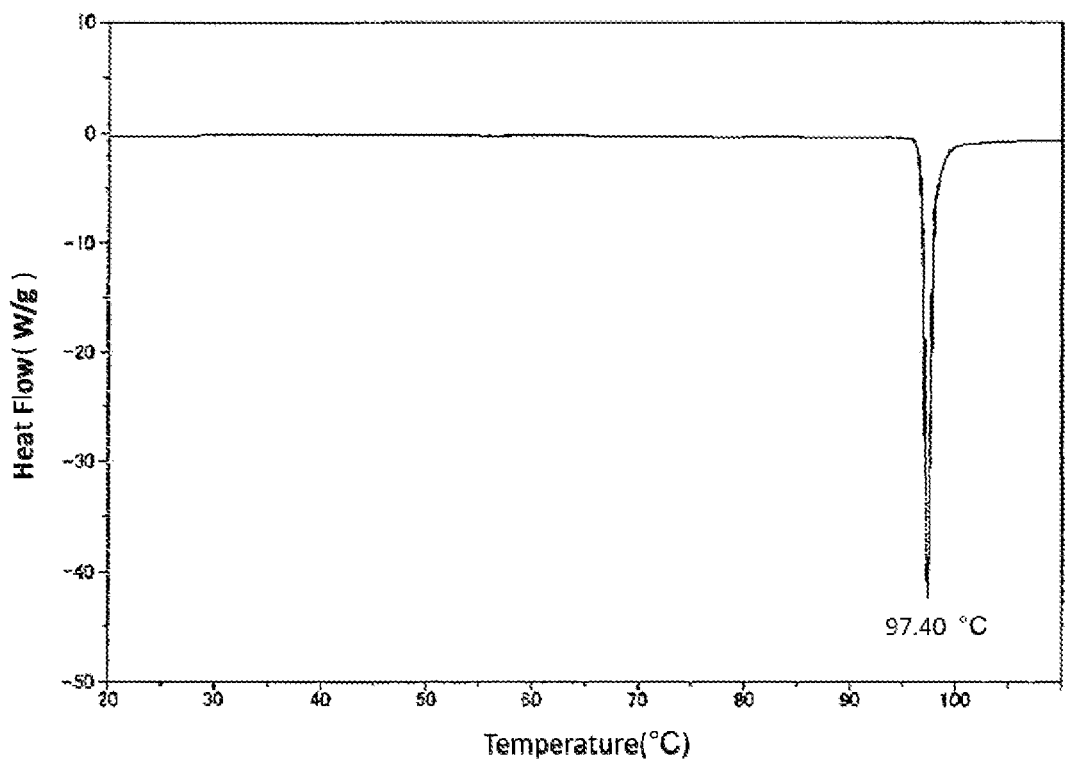
FIG. 2 is a graph showing the results of performing a DSC measurement of type II crystals of rotigotine free form.

First, the type I crystals and type II crystals of rotigotine (free form) were heated at a rate of temperature rise of 10° C./min from 10° C. to 120° C. with a differential scanning calorimeter ("Q-2000," manufactured by TA Instruments), thereby performing DSC measurement. The peaks observed in the obtained thermograms were used to determine the endothermic melting point peaks (melting points), which were 78.56° C. for type I and 97.40° C. for type II. FIG. 1 shows the DSC measurement results for the type I crystals of rotigotine free form, and FIG. 2 shows the DSC measurement results for the type II crystals of rotigotine free form.

Next, an end portion of each of the patches immediately after production and 6 months after production (the patch was sealed in an aluminum laminate bag and stored at room temperature (about 25° C.) for 6 months) was cut out, and a microspatula was used to peel off from the backing layer the adhesive agent layer, which was sealed in a hermetic pan. This was subjected to DSC measurement while being heated at a rate of temperature rise of 10° C./min from 10° C. to 120° C. with the above differential scanning calorimeter. The endothermic melting point peaks at around 78.56° C. and 97.4° C. and baseline shift were observed. Note that, in the thermogram obtained by DSC measurement, an endothermic melting point peak observed indicates that the drug contained in the adhesive agent layer is crystalline, a baseline shift observed indicates that the drug contained in the adhesive agent layer amorphous, and the situation where none of them is observed indicates that the drug contained in the adhesive agent layer is in a complete dissolved form.

Example 1

First, to an appropriate amount of solvent (absolute ethanol and toluene), 9.0 parts by mass of rotigotine (free form), 14.5 parts by mass of styrene-isoprene-styrene block copolymer, 6.2 parts by mass of polyisobutylene, 45.7 parts by mass of alicyclic saturated hydrocarbon resin, 16.6 parts by mass of liquid paraffin, 5 parts by mass of octyldodecanol, and 3 parts by mass of cross-linked polyvinylpyrrolidone (cross-linked PVP) were added and mixed to obtain an adhesive agent layer composition. Next, the obtained adhesive agent layer composition was applied on a release liner (polyethylene terephthalate film subjected to release treatment), and the solvent was removed by drying to a mass per unit area of 50 g/m$^2$, thereby forming an adhesive agent layer. A backing layer (polyethylene terephthalate film) was stacked on the surface of the obtained adhesive agent layer opposite to the release liner to obtain a patch formed of a stack of backing layer/adhesive agent layer/release liner in this order.

Examples 2 and 3 and Comparative Examples 1 to 3

Each patch was obtained in the same manner as in Example 1 except that the composition of the adhesive agent layer composition was changed to the compositions shown in Table 1 below.

The patches obtained in Examples 1 to 3 and Comparative Examples 1 to 3 were subjected to a skin permeation test and a crystal precipitation evaluation (3 days after production). Table 1 shows the results together with the compositions (excluding the solvent) of the adhesive agent layer compositions of Examples and Comparative Examples.

TABLE 1

| | Comparative Example | | | Example | | |
|---|---|---|---|---|---|---|
| | 1 | 2 | 3 | 1 | 2 | 3 |
| Adhesive Agent Layer Composition [Parts by Mass] | | | | | | |
| Rotigotine | 9 | 9 | 9 | 9 | 9 | 9 |
| Styrene-Isoprene-Styrene Block Copolymer | 15.9 | 15.1 | 14.9 | 14.5 | 14.2 | 13.1 |
| Polyisobutylene | 6.8 | 6.4 | 6.3 | 6.2 | 6.1 | 5.7 |
| Alicyclic Saturated Hydrocarbon Resin | 50.1 | 47.3 | 46.8 | 45.7 | 44.5 | 42.2 |
| Liquid Paraffin | 18.2 | 17.2 | 17.0 | 16.6 | 16.2 | 15.0 |
| Octyldodecanol | — | 5 | 5 | 5 | 5 | 5 |
| Cross-Linked PVP | — | — | 1 | 3 | 5 | 10 |
| Total | 100 | 100 | 100 | 100 | 100 | 100 |
| Evaluation | | | | | | |
| Maximum Rate of Skin Permeation (Jmax) [µg/cm$^2$/hr] | 11.7 | 17.2 | 18.4 | 15.6 | 13.5 | 12.9 |
| Crystal Precipitation Evaluation (Day 3) | B | B | B | A | A | A |

Figure 3:
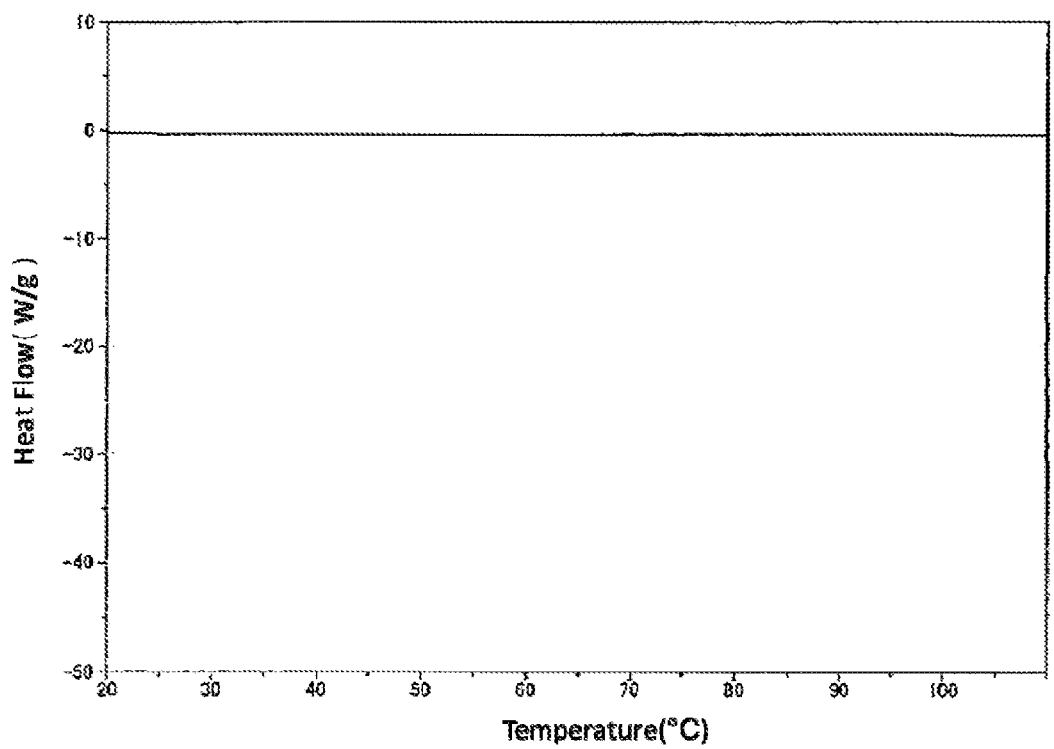
FIG. 3 is a graph showing the results of performing a DSC measurement on the adhesive agent layer of the patch obtained in Example 3 after 6 months from production.

In the patches obtained in Examples 1 to 3, crystalline and amorphous particles were not confirmed even after 3 days from production. In addition, when the DSC measurement of adhesive agent layer was performed on the patches obtained in Examples 1 to 3, no endothermic melting point peak derived from crystals and no baseline shift due to glass transition derived from amorphous substances were observed immediately after production and 6 months after production, but it was confirmed that rotigotine was contained in a completely dissolved form in the adhesive agent layer. FIG. 3 shows the results of performing a DSC measurement on the adhesive agent layer of the patch obtained in Example 3 after 6 months from production. On the other hand, in the patches obtained in Comparative Examples 1 to 3, precipitation of crystals was confirmed immediately after production. In addition, when DSC measurement of patch adhesive agent layer was performed on the patches immediately after production obtained in Comparative Examples 1 to 3, an endothermic melting point peak derived from crystals was observed.

Comparative Examples 4 to 11

Each patch was obtained in the same manner as in Example 1 except that the composition of the adhesive agent layer composition was changed to the compositions shown in Table 2 below. In Table 2, the hydrogenated rosin ester used was "KE-311 (manufactured by Arakawa Chemical Industries, Ltd.)," the aminoalkyl methacrylate copolymer E used was "EUDRAGIT (manufactured by Evonik)," the vinyl acetate vinyl pyrrolidone copolymer used was "Kollidon VA-64 (manufactured by BASF)," and the polyvinyl caprolactam. polyvinyl acetate. polyethylene glycol graft copolymer used was "Soluplus (manufactured by BASF)."

The patches obtained in Comparative Examples 4 to 11 were subjected to a skin permeation test and a crystal precipitation evaluation (3 days after production). Table 2 shows the results together with the compositions (excluding the solvent) of the adhesive agent layer compositions of Comparative Examples. In Table 2, the maximum rate of skin permeation is indicated by a value when the maximum rate of skin permeation in Example 3 above is set to 100, and Table 2 also shows, as a reference, the composition of the adhesive agent layer composition of Example 3 and the results of the skin permeation test and the crystal precipitation evaluation.

TABLE 2

| | Example | Comparative Example | | | | | | | |
|---|---|---|---|---|---|---|---|---|---|
| | 3 | 4 | 5 | 6 | 7 | 8 | 9 | 10 | 11 |
| Adhesive Agent Layer Composition [Parts by Mass] | | | | | | | | | |
| Rotigotine | 9 | 9 | 9 | 9 | 9 | 9 | 9 | 9 | 9 |
| Styrene-Isoprene-Styrene Block Copolymer | 13.1 | 13.1 | 13.1 | 14.2 | 14.2 | 14.2 | 13.1 | 14.2 | 13.1 |
| Polyisobutylene | 5.7 | 5.7 | 5.7 | 6.1 | 6.1 | 6.1 | 5.7 | 6.1 | 5.7 |
| Alicyclic Saturated Hydrocarbon Resin | 42.2 | — | 42.2 | 44.5 | 44.5 | 44.5 | 42.2 | 44.5 | 42.2 |
| Hydrogenated Rosin Ester | — | 42.2 | — | — | — | — | — | — | — |
| Liquid Paraffin | 15.0 | 15.0 | 15.0 | 16.2 | 16.2 | 16.2 | 15.0 | 16.2 | 15.0 |
| Octyldodecanol | 5 | 5 | 5 | 5 | 5 | 5 | 5 | 5 | 5 |
| Cross-Linked PVP | 10 | 10 | — | — | — | — | — | — | — |
| Non-Cross-Linked PVP | — | — | 10 | — | — | — | — | — | — |
| Aminoalkyl Methacrylate Copolymer E | — | — | — | 5 | — | — | — | — | — |
| Carboxymethyl Cellulose | — | — | — | — | 5 | — | — | — | — |
| Vinyl Acetate•Vinyl Pyrrolidone Copolymer | — | — | — | — | — | 5 | 10 | — | — |
| Polyvinyl Caprolactam•Polyvinyl Acetate•Polyethylene Glycol Graft Copolymer | — | — | — | — | — | — | — | 5 | 10 |
| Total | 100 | 100 | 100 | 100 | 100 | 100 | 100 | 100 | 100 |
| Evaluation | | | | | | | | | |
| Maximum Rate of Skin Permeation (Jmax) [As Compared with Example 3] | 100 | 42.4 | 65.2 | 65.1 | 44.2 | 72.9 | 58.1 | 45.0 | 27.1 |
| Crystal Precipitation Evaluation (Day 3) | A | A | A | A | A | A | A | A | A |

Reference Examples 1 to 21

Each patch was obtained in the same manner as in Example 1 except that the composition of the adhesive agent layer composition was changed to the compositions shown in Table 3 below. As the absorption enhancers shown in Table 3, the absorption enhancers shown in Table 4 below were used.

Table 3 shows the compositions (excluding the solvent) of the adhesive agent layer compositions in Reference Examples 1 to 21. In addition, Table 4 shows the results of skin permeation test and crystal precipitation evaluation (3 days after production) of the patches obtained in Reference Examples 1 to 21 together with the absorption enhancers used in Reference Examples.

TABLE 3

| Adhesive Agent Layer Composition [Parts by Mass] | Reference Examples 1 to 21 |
|---|---|
| Rotigotine | 9 |
| Styrene-Isoprene-Styrene Block Copolymer | 15.4 |
| Polyisobutylene | 6.6 |
| Alicyclic Saturated Hydrocarbon Resin | 48.4 |
| Liquid Paraffin | 17.6 |
| Absorption Enhancer | 3 |
| Total | 100 |

TABLE 4

| Reference Example | Absorption Enhancer | Maximum Rate of Skin Permeation (Jmax) [µg/cm²/hr] | Crystal Precipitation Evaluation (Day 3) |
|---|---|---|---|
| 1 | Isopropanol (C3) | 13.6 | B |
| 2 | Hexyl Alcohol (C6) | 13.2 | B |
| 3 | Lauryl Alcohol (C12) | 18.6 | B |
| 4 | Myristyl Alcohol (C14) | 14.2 | B |
| 5 | Cetyl Alcohol (C16) | 12.3 | B |
| 6 | Stearyl Alcohol (C18) | 12.7 | B |
| 7 | Isostearyl Alcohol (C18) | 12.9 | B |
| 8 | Octyldodecanol (20) | 17.6 | B |
| 9 | Oleyl Alcohol (C18, Unsaturated) | 15.1 | B |
| 10 | Diethanolamine | 10.1 | B |
| 11 | Triisopropanolamine | 5.7 | B |
| 12 | Diisopropanolamine | 5.7 | B |
| 13 | Isopropanolamine | 6.8 | B |
| 14 | Lauryldimethylaminoacetic Acid Betaine | 11.0 | B |
| 15 | Glycerol Monooleate | 11.8 | B |
| 16 | Sorbitan Laurate | 11.0 | B |
| 17 | Alginic Acid | 11.4 | B |
| 18 | Sorbic Acid | 5.7 | A |

TABLE 4-continued

| Reference Example | Absorption Enhancer | Maximum Rate of Skin Permeation (Jmax) [µg/cm$^2$/hr] | Crystal Precipitation Evaluation (Day 3) |
|---|---|---|---|
| 19 | Palmitic Acid | 7.1 | A |
| 20 | Lactic Acid | 4.5 | A |
| 21 | Dimethylsulfoxide | 10.8 | B |

As shown in the DSC measurement results as well as in Table 1 and FIGS. 1 to 3, it was confirmed that, in the patch of the present invention, the drug was contained in the adhesive agent layer in a dissolved form immediately after production, precipitation of crystals was suppressed even after storage, and a high level of skin permeability was achieved.

On the other hand, when no cross-linked polyvinylpyrrolidone was contained or when the content of the cross-linked polyvinylpyrrolidone was out of the range according to the present invention (Comparative Examples 1 to 3), crystals of rotigotine were precipitated, and when a solubilizer or the like conventionally known to have a function of dissolving crystals was used instead of cross-linked polyvinylpyrrolidone (Comparative Examples 5 to 11), the precipitation of rotigotine crystals was not confirmed, but the skin permeability of rotigotine was significantly reduced, as shown in Table 2. In addition, when a hydrogenated rosin ester as a tackifier was used instead of the alicyclic saturated hydrocarbon resin (Comparative Example 4), the skin permeability of rotigotine was significantly reduced. Moreover, when no aliphatic alcohol was contained (Comparative Example 1), it was confirmed that the skin permeability of rotigotine was significantly reduced, and in addition, it was suggested that when another absorption enhancer was used instead of the aliphatic alcohol (Reference Examples 10 to 21), the skin permeability of rotigotine was reduced.

Examples 4 to 6

Each patch was obtained in the same manner as in Example 1 except that the composition of the adhesive agent layer composition was changed to the compositions shown in Table 5 below. The patches obtained in Examples 4 to 6 were subjected to a skin permeation test and a crystal precipitation evaluation (6 months after production). Table 5 shows the results together with the compositions (excluding the solvent) of the adhesive agent layer compositions of Examples.

TABLE 5

| | Example 4 | Example 5 | Example 6 |
|---|---|---|---|
| Adhesive Agent Layer Composition [Parts by Mass] | | | |
| Rotigotine | 9 | 9 | 9 |
| Styrene-Isoprene-Styrene Block Copolymer | 13.3 | 13.2 | 13.6 |
| Polyisobutylene | 5.7 | 5.6 | 5.9 |
| Alicyclic Saturated Hydrocarbon Resin | 41.55 | 41.45 | 42.70 |
| Liquid Paraffin | 15.2 | 15.1 | 15.5 |
| Octyldodecanol | 5 | 5 | 3 |

TABLE 5-continued

| | Example 4 | Example 5 | Example 6 |
|---|---|---|---|
| Cross-Linked PVP | 10 | 10 | 10 |
| Stabilizer (2-Mercaptobenzimidazole) | 0.25 | 0.65 | 0.30 |
| Total | 100 | 100 | 100 |
| Evaluation | | | |
| Maximum Rate of Skin Permeation (Jmax) [µg/cm$^2$/hr] | 13.3 | 12.7 | 13.7 |
| Crystal Precipitation Evaluation (Month 6) | A | A | A |

As shown in Table 5, in the patches obtained in Examples 4 to 6, crystalline and amorphous particles were not confirmed even after 6 months from the production.

Examples 7 and 8 and Comparative Example 12

Each patch was obtained in the same manner as in Example 1 except that the composition of the adhesive agent layer composition was changed to the compositions shown in Table 6 below. In Table 6, the terpene-based resin used was "YS RESIN PX1150N (manufactured by YASUHARA CHEMICAL CO., LTD.)," and the hydrogenated rosin ester used was "KE-311 (manufactured by Arakawa Chemical Industries, Ltd.)."

The patches obtained in Examples 7 and 8 and Comparative Example 12 were subjected to a skin permeation test and a crystal precipitation evaluation (after 6 months of production). In addition, in the crystal precipitation evaluation, the surface of the adhesive agent layer after storage was observed only visually, and the condition of the surface of each adhesive agent layer was evaluated based on the following criteria:

A: no particles (crystalline particles and amorphous particles) are visually observed, and B: particles (crystalline particles and/or amorphous particles) are visually observed Table 6 shows the results together with the compositions (excluding the solvent) of the adhesive agent layer compositions of Examples and Comparative Examples.

TABLE 6

| | Example 7 | Example 8 | Comparative Example 12 |
|---|---|---|---|
| Adhesive Agent Layer Composition [Parts by Mass] | | | |
| Rotigotine | 9 | 9 | 9 |
| Styrene-Isoprene-Styrene Block Copolymer | 13.3 | 13.3 | 13.3 |
| Polyisobutylene | 5.7 | 5.7 | 5.7 |
| Alicyclic Saturated Hydrocarbon Resin | 41.5 | — | — |

TABLE 6-continued

|  | Example 7 | Example 8 | Comparative Example 12 |
|---|---|---|---|
| Terpene-Based Resin | — | 41.5 | — |
| Hydrogenated Rosin Ester | — | — | 41.5 |
| Liquid Paraffin | 15.2 | 15.2 | 15.2 |
| Octyldodecanol | 5 | 5 | 5 |
| Cross-Linked PVP | 10 | 10 | 10 |
| Stabilizer (2-Mercaptobenzimidazole) | 0.3 | 0.3 | 0.3 |
| Total | 100 | 100 | 100 |
| Evaluation | | | |
| Maximum Rate of Skin Permeation (Jmax) [µg/cm$^2$/hr] | 15.8 | 13.6 | 6.7 |
| Crystal Precipitation Evaluation (Month 6) | A | A | A |

As shown in Table 6, in the patches obtained in Examples 7 and 8 using petroleum-based resins and terpene-based resins, it was confirmed that the precipitation of crystals was suppressed even after storage, and that a high level of skin permeability was achieved. Meanwhile, when the hydrogenated rosin ester was used (Comparative Example 12), it was confirmed that the skin permeability of rotigotine was significantly reduced as in Comparative Example 4.

Examples 9 to 12

Each patch was obtained in the same manner as in Example 1 except that the composition of the adhesive agent layer composition was changed to the compositions shown in Table 7 below. The patches obtained in Examples 9 to 12 were subjected to a skin permeation test and a crystal precipitation evaluation (3 days after production). Note that the crystal precipitation evaluation was performed in the same manner as in Examples 7 to 8 and Comparative Example 12 except that the storage period was set to 3 days. Table 7 shows the results together with the compositions (excluding the solvent) of the adhesive agent layer compositions of Examples.

TABLE 7

|  | Example 9 | Example 10 | Example 11 | Example 12 |
|---|---|---|---|---|
| Adhesive Agent Layer Composition [Parts by Mass] | | | | |
| Rotigotine | 9 | 9 | 9 | 9 |
| Styrene-Isoprene-Styrene Block Copolymer | 13.3 | 13.3 | 13.3 | 13.3 |
| Polyisobutylene | 5.7 | 5.7 | 5.7 | 5.7 |
| Alicyclic Saturated Hydrocarbon Resin | 41.8 | 41.8 | 41.8 | 41.8 |
| Liquid Paraffin | 15.2 | 15.2 | 15.2 | 15.2 |
| Octyldodecanol | 5 | — | — | — |
| Isostearyl alcohol | — | 5 | — | — |
| Hexyldecanol | — | — | 5 | — |
| Lauryl alcohol | — | — | — | 5 |
| Cross-Linked PVP | 10 | 10 | 10 | 10 |
| Total | 100 | 100 | 100 | 100 |

TABLE 7-continued

|  | Example 9 | Example 10 | Example 11 | Example 12 |
|---|---|---|---|---|
| Evaluation | | | | |
| Maximum Rate of Skin Permeation (Jmax) [µg/cm$^2$/hr] | 12.5 | 13.6 | 13.7 | 13.7 |
| Crystal Precipitation Evaluation (Day 3) | A | A | A | A |

As shown in Table 7, in the patches obtained in Examples 9 to 12 using an aliphatic alcohol, it was confirmed that precipitation of crystals was suppressed even after storage, and that a high level of skin permeability was achieved.

Examples 13 and 14

Each patch was obtained in the same manner as in Example 1 except that the composition of the adhesive agent layer composition was changed to the compositions shown in Table 8 below. The patches obtained in Examples 13 and 14 and the patches obtained in Example 6 above were subjected to a skin permeation test and a crystal precipitation evaluation (3 days after production). Note that, in the skin permeation test, a frozen human skin slice was thawed at room temperature in place of the fat-removed skin piece of the body of a hairless mouse to remove subcutaneous fat, and then a fat-removed skin piece cut to a thickness of about 500 µm with a dermatome was used. In addition, the crystal precipitation evaluation was performed in the same manner as in Examples 7 to 8 and Comparative Example 12 except that the storage period was set to 3 days. Table 8 shows the results together with the compositions (excluding the solvent) of the adhesive agent layer compositions of Examples. In Table 8, the maximum rate of skin permeation is indicated by a value when the maximum rate of skin permeation in Example 6 is set to 100, and Table 8 also shows, as a reference, the composition of the adhesive agent layer composition of the same Example 6.

TABLE 8

|  | Example 6 | Example 13 | Example 14 |
|---|---|---|---|
| Adhesive Agent Layer Composition [Parts by Mass] | | | |
| Rotigotine | 9 | 9 | 9 |
| Styrene-Isoprene-Styrene Block Copolymer | 13.6 | 13.2 | 12.9 |
| Polyisobutylene | 5.9 | 5.7 | 5.5 |
| Alicyclic Saturated Hydrocarbon Resin | 42.7 | 41.7 | 40.6 |
| Liquid Paraffin | 15.5 | 15.1 | 14.7 |
| Octyldodecanol | 3 | 5 | 7 |
| Cross-Linked PVP | 10 | 10 | 10 |
| Stabilizer (2-Mercaptobenzimidazole) | 0.3 | 0.3 | 0.3 |
| Total | 100 | 100 | 100 |
| Evaluation | | | |
| Maximum Rate of Skin Permeation (Human, Jmax) [As Compared with Example 6] | 100 | 93.6 | 92.6 |
| Crystal Precipitation Evaluation (Day 3) | A | A | A |

As shown in Table 8, in the patches obtained in Examples 13 and 14, it was confirmed that the precipitation of crystals was suppressed even after storage, and that a high level of skin permeability was achieved, as in the patch obtained in Example 6.

INDUSTRIAL APPLICABILITY

As described above, the present invention makes it possible to provide a rotigotine-containing patch containing rotigotine and/or a pharmaceutically acceptable salt thereof in a dissolved form in an adhesive agent layer and having excellent stability over time and skin permeability of rotigotine.

The invention claimed is:

1. A rotigotine-containing patch comprising: a backing layer;
and an adhesive agent layer, wherein the adhesive agent layer contains rotigotine and/or a pharmaceutically acceptable salt thereof,
the adhesive agent layer further contains:
a styrene-based thermoplastic elastomer;
a petroleum-based resin and/or a terpene-based resin;
an aliphatic alcohol; and
a cross-linked polyvinylpyrrolidone;
wherein the petroleum-based resin is an alicyclic saturated hydrocarbon resin,
the terpene-based resin is a pinene polymer, and
in the adhesive agent layer, a mass ratio of a content of the rotigotine and/or the pharmaceutically acceptable salt thereof in terms of rotigotine free form and a content of the cross-linked polyvinylpyrrolidone (content of the rotigotine and/or the pharmaceutically acceptable salt thereof in terms of rotigotine free form : content of the cross-linked polyvinylpyrrolidone) is 10:3 to 1:3.

2. The rotigotine-containing patch according to claim 1, wherein the adhesive agent layer contains the rotigotine and/or the pharmaceutically acceptable salt thereof in a dissolved form.

3. The rotigotine-containing patch according to claim 1, wherein the aliphatic alcohol has 12 to 23 carbon atoms.

4. The rotigotine-containing patch according to claim 1, wherein the content of the rotigotine and/or the pharmaceutically acceptable salt thereof in the adhesive agent layer in terms of rotigotine free form is 5 to 15% by mass relative to a total mass of the adhesive agent layer.

5. The rotigotine-containing patch according to claim 1, wherein a content of the petroleum-based resin and/or the terpene-based resin in the adhesive agent layer is 5 to 80% by mass relative to the total mass of the adhesive agent layer.

6. The rotigotine-containing patch according to claim 1, wherein a content of the aliphatic alcohol in the adhesive agent layer is 1 to 15% by mass relative to the total mass of the adhesive agent layer.

7. The rotigotine-containing patch according to claim 1, wherein the adhesive agent layer further contains a stabilizer.

* * * * *